(12) United States Patent
Arcand (10) Patent No.: US 10,265,152 B2
(45) Date of Patent: Apr. 23, 2019

(54) PELVIC IMPLANT SIZING SYSTEMS AND METHODS

(71) Applicant: Boston Scientific Scimed, Inc., Maple Grove, MN (US)

(72) Inventor: Benjamin Y Arcand, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 451 days.

(21) Appl. No.: 13/652,145

(22) Filed: Oct. 15, 2012

(65) Prior Publication Data

US 2013/0096371 A1    Apr. 18, 2013

Related U.S. Application Data

(60) Provisional application No. 61/546,949, filed on Oct. 13, 2011, provisional application No. 61/546,877, filed on Oct. 13, 2011.

(51) Int. Cl.
*A61F 2/00* (2006.01)

(52) U.S. Cl.
CPC .... *A61F 2/0063* (2013.01); *A61F 2002/0068* (2013.01)

(58) Field of Classification Search
CPC ....... A61B 17/8085; A61F 2002/30136; A61F 2/0004; A61F 2/0031
See application file for complete search history.

(56) References Cited

U.S. PATENT DOCUMENTS

| | | |
|---|---|---|
| 2,738,790 A | 3/1956 | Todt et al. |
| 3,124,136 A | 3/1964 | Usher |
| 3,311,110 A | 3/1967 | Singerman et al. |
| 3,580,313 A | 5/1971 | McKnight |
| 3,763,860 A | 10/1973 | Clarke |
| 3,858,783 A | 1/1975 | Kapitanov et al. |
| 3,924,633 A | 12/1975 | Cook et al. |
| 3,995,619 A | 12/1976 | Glatzer |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |

(Continued)

FOREIGN PATENT DOCUMENTS

| | | |
|---|---|---|
| AU | 2002241673 | 11/2005 |
| CA | 2404459 C | 8/2005 |

(Continued)

OTHER PUBLICATIONS

Amundsen et al., "Anatomical correction of vaginal vault prolapse by uterosacral ligament fixation in women who also require a pubovaginal sling," the J. of Urology, vol. 169, 1770-1776, May 2003.

(Continued)

*Primary Examiner* — Christine H Matthews
(74) *Attorney, Agent, or Firm* — Brake Hughes Bellermann LLP (57) ABSTRACT

Various embodiments of a mesh or implant sizing system are provided. An implant can include a gauging portion included with a support portion of the implant, to assist a surgeon in determining what size implant to insert into the pocket created in a tissue plane of the patient.

17 Claims, 4 Drawing Sheets

(56) References Cited

U.S. PATENT DOCUMENTS

| | | |
|---|---|---|
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,865,031 A | 9/1989 | O'Keeffe |
| 4,873,976 A | 10/1989 | Schreiber |
| 4,932,962 A | 6/1990 | Yoon et al. |
| 4,969,892 A | 11/1990 | Burton et al. |
| 5,013,316 A | 5/1991 | Goble et al. |
| 5,053,043 A | 10/1991 | Gottesman et al. |
| 5,085,661 A | 2/1992 | Moss |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,269,783 A | 12/1993 | Sander |
| 5,281,237 A | 1/1994 | Gimpelson |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,571,139 A | 11/1996 | Jenkins, Jr. |
| 5,591,206 A | 1/1997 | Moufarrege |
| 5,628,756 A | 5/1997 | Barker, Jr. et al. |
| 5,643,320 A | 7/1997 | Lower et al. |
| 5,669,935 A | 9/1997 | Rosenman et al. |
| 5,683,349 A | 11/1997 | Makower et al. |
| 5,709,708 A | 1/1998 | Thal |
| 5,725,541 A | 3/1998 | Anspach, III et al. |
| 5,741,282 A | 4/1998 | Anspach, III et al. |
| 5,807,403 A | 9/1998 | Beyar et al. |
| 5,842,478 A | 12/1998 | Benderev et al. |
| 5,919,232 A | 7/1999 | Chaffringeon et al. |
| 5,922,026 A | 7/1999 | Chin |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,027,523 A | 2/2000 | Schmieding |
| 6,036,701 A | 3/2000 | Rosenman |
| 6,042,583 A | 3/2000 | Thompson et al. |
| 6,048,351 A | 4/2000 | Gordon et al. |
| 6,071,290 A | 6/2000 | Compton |
| 6,074,341 A | 6/2000 | Anderson et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,241,736 B1 | 6/2001 | Sater et al. |
| 6,328,744 B1 | 12/2001 | Harari et al. |
| 6,387,041 B1 | 5/2002 | Harari et al. |
| 6,406,480 B1 | 6/2002 | Beyar et al. |
| 6,414,179 B1 | 7/2002 | Banville |
| 6,482,214 B1 | 11/2002 | Sidor, Jr. et al. |
| 6,494,906 B1 | 12/2002 | Owens |
| 6,506,190 B1 | 1/2003 | Walshe |
| 6,575,897 B1 | 6/2003 | Ory |
| 6,592,515 B2 | 7/2003 | Thierfelder |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,284 B1 | 10/2003 | Rousseau et al. |
| 6,648,921 B2 | 11/2003 | Anderson |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,884,212 B2 | 4/2005 | Thierfelder et al. |
| 6,908,473 B2 | 6/2005 | Skiba et al. |
| 6,911,003 B2 | 6/2005 | Anderson et al. |
| 6,936,052 B2 | 8/2005 | Gellman et al. |
| 6,953,428 B2 | 10/2005 | Gellman et al. |
| 6,971,986 B2 | 12/2005 | Staskin et al. |
| 6,974,462 B2 | 12/2005 | Sater |
| 6,981,944 B2 | 1/2006 | Jamiolkowski |
| 6,981,983 B1 | 1/2006 | Rosenblatt et al. |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,558 B2 | 7/2006 | Gellman et al. |
| 7,083,637 B1 | 8/2006 | Tannhauser |
| 7,087,065 B2 | 8/2006 | Ulmsten et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,226,408 B2 | 6/2007 | Harari et al. |
| 7,229,404 B2 | 6/2007 | Bouffier |
| 7,229,453 B2 | 6/2007 | Anderson |
| 7,235,043 B2 | 6/2007 | Gellman et al. |
| 7,299,803 B2 | 11/2007 | Kovac |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke et al. |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,637,860 B2 | 12/2009 | MacLean |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,766,926 B2 | 8/2010 | Bosely et al. |
| 7,981,024 B2 | 7/2011 | Levy |
| 8,172,745 B2 | 5/2012 | Rosenblatt |
| 2002/0007222 A1 | 1/2002 | Desai |
| 2002/0028980 A1 | 3/2002 | Thierfelder et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0010929 A1 | 1/2003 | Prieve et al. |
| 2003/0065402 A1 | 4/2003 | Anderson et al. |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Krammerer |

(56) References Cited

U.S. PATENT DOCUMENTS

| | | |
|---|---|---|
| 2005/0000523 A1 | 1/2005 | Beraud |
| 2005/0004427 A1 | 1/2005 | Cervigni |
| 2005/0004576 A1 | 1/2005 | Benderev |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0229596 A1 | 10/2006 | Weiser et al. |
| 2007/0015953 A1 | 1/2007 | MacLean |
| 2007/0161850 A1* | 7/2007 | Harari et al. ............ 600/30 |
| 2007/0173864 A1 | 7/2007 | Chu |
| 2008/0039678 A1 | 2/2008 | Montpetit et al. |
| 2008/0140218 A1 | 6/2008 | Staskin et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0099409 A1* | 4/2009 | Luehrs et al. ............ 600/37 |
| 2009/0221868 A1 | 9/2009 | Evans |
| 2009/0259092 A1* | 10/2009 | Ogdahl et al. ............ 600/30 |
| 2010/0022822 A1 | 1/2010 | Walshe |
| 2010/0179575 A1 | 7/2010 | Von Pechmann et al. |
| 2010/0261950 A1 | 10/2010 | Lund |
| 2010/0280627 A1 | 11/2010 | Hanes, II |
| 2011/0124954 A1 | 5/2011 | Odhahl |
| 2011/0174313 A1 | 7/2011 | Von Pechmann et al. |
| 2012/0016185 A1 | 1/2012 | Sherts et al. |

FOREIGN PATENT DOCUMENTS

| | | |
|---|---|---|
| DE | 2305815 | 2/1973 |
| DE | 4220283 C2 | 5/1994 |
| DE | 19544162 C1 | 4/1997 |
| EP | 0632999 A1 | 1/1992 |
| EP | 1060714 A3 | 9/2002 |
| FR | 2852813 A1 | 1/2004 |
| IT | 1299162 | 4/1998 |
| SU | 1225547 A1 | 4/1986 |
| SU | 1342486 A1 | 10/1987 |
| WO | WO9317635 A1 | 9/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9835606 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO1999/059477 | 11/1999 |
| WO | WO9959477 A1 | 11/1999 |
| WO | WO0064370 A1 | 2/2000 |
| WO | WO0013601 A1 | 3/2000 |
| WO | WO0040158 A2 | 7/2000 |
| WO | WO0057812 A1 | 10/2000 |
| WO | WO0074633 A2 | 12/2000 |
| WO | WO0106951 A1 | 2/2001 |
| WO | WO0139670 A1 | 6/2001 |
| WO | WO0156499 A1 | 8/2001 |
| WO | WO0234124 A2 | 5/2002 |
| WO | WO02071953 A2 | 9/2002 |
| WO | WO02078552 A1 | 10/2002 |
| WO | WO03017848 A1 | 3/2003 |
| WO | WO0303778 A1 | 4/2003 |
| WO | WO03028585 A2 | 4/2003 |
| WO | WO03037215 A2 | 5/2003 |
| WO | WO03041613 A1 | 5/2003 |
| WO | WO03068107 A1 | 8/2003 |
| WO | WO03092546 A2 | 11/2003 |
| WO | WO03096929 A1 | 11/2003 |
| WO | WO2004012626 A1 | 2/2004 |
| WO | WO2005079702 A1 | 9/2005 |
| WO | WO2005122954 A1 | 12/2005 |
| WO | WO2006108145 A1 | 10/2006 |
| WO | WO2007011341 A1 | 1/2007 |
| WO | WO2007016083 A1 | 2/2007 |
| WO | WO2007027592 A2 | 3/2007 |
| WO | WO2007081955 A1 | 7/2007 |
| WO | WO2007097994 | 8/2007 |
| WO | WO2007146784 A2 | 12/2007 |
| WO | WO2007149348 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |
| WO | WO2011/082350 | 7/2011 |

OTHER PUBLICATIONS

Cervigni et al., "The use of synthetics in the treatment of pelvic organ prolapse," Current Opinion in Urology 2011, 11:429-435.

Eglin et al., Transobturator subvesical mesh: tolerance and short-term results of a 103 case continuous series, Service de gynecologic clinque Dhampeau 32 (Nov. 2002).

Farnsworth, B. N., "Posterior intravaginal slingplasty (infracoccygeal sacropexy) for severe posthysterectomy and vaginal vault prolapse—a preliminary report on efficacy and safety," Int. Urogynecol J (2002) 13:4-8.

Heit et al., "Predicting treatment choice for patients with pelvic organ prolapse," The Am. College of Obstet. & Gyn., vol. 101, No. 6, Jun. 2003.

Julian, Thomas, "The efficacy of Mariex mesh in the repair of severe, recurrent vaginal prolapse of the anterior midvaginal wall," Am. J. Obstet. Gynecol. vol. 175, No. 6, pp. 1471-1476 (1996).

Karram et al., "Surgical Treatment of Vaginal Vault Prolapse," Urogynecology and reconstructive pelvic surgery, Mosby (1999).

Luber, et al., "The demographics of pelvic floor disorders: current observations and future projections," Am. J. Obstet. Gynecol. vol. 184, No. 7, pp. 1496-1504 (2001).

Mage, PH., "L-interposition d'un treillis synthetique dans la cure par voie vaginale des prolapses genitaux," Technique chirurgicale, J. Gynecol. Obstet. Reprod. 1999:28:825-829.

Marchionni, et al., "True incidence of vaginal vault prolapse: thirteen years of experience," J. of Reproductive Medicine, vol. 44, No. 8, pp. 679-685 (1999).

Migliari et al., "Tension-free vaginal mesh repair for anterior vaginal wall prolapse," Eur. Urol. 2000;38:151-155.

Morley et al., "Sacrospinous ligament fixation for eversion of the vagina," Am. J. Obstet. Gynecol., vol. 158, No. 4, pp. 871-881 (1988).

Nicita, Giulio, "A new operation for genitourinary prolapse," The Journal of Urology, vol. 160, 741-745 (1998).

Paraiso, et al., "Laparoscopic surgery for enterocele, vaginal apex prolapse and rectocele," Int. Urogynecol. J. 10:223-239 (1990).

Paraiso, et al., "Pelvic support defects and visceral and sexual function in women treated with sacrospinous ligament suspension and pelvic reconstruction," Am. J. Obstet. & Gyne. vol. 175, No. 6 (1996).

Petros, P.E., "Vault Prolapse II: restoration of dynamic vaginal supports by infracoccygeal sacropexy, and axial day-case vaginal procedure," Int. Urogynecol. J. (2001) 12:296-303.

Petros, et al., "The posterior fornix syndrome: a multiple symptom complex of pelvic pain and abnormal urinary symptoms deriving from laxity in the posterior fornix of vagina," Scand. J. Urol Nephrol. Suppl. No. 153, pp. 89-95 (1993).

(56) References Cited

OTHER PUBLICATIONS

Richter, Kurt, "Massive eversion of the vagina: pathogenesis, diagnosis, and therapy of the 'true' prolapse of the vaginal stump," Clinical Obstet. & Gyne., vol. 25, No. 4, pp. 897-911 (1982).

Sanz et al., "Modification abdominal sacrocolpopexy using a suture anchor system," Journal of Reproductive Medicine, vol. 48, No. 7, pp. 496-501 (2003).

Subak et al., "Cost of pelvic organ prolapse surgery in the United States," Am. College Obstet. & Gyne., vol. 98, No. 4, pp. 464-452 (2001).

Sullivan et al., "Total pelvic mesh repair," Dis Colon Rectum, vol. 44, No. 6 pp. 857-864 (2001).

Swift et al., "Case-control study of etiologic factors in the development of severe pelvic organ prolapse," Int. Urogynecol. J. 12:187-192 (2001).

Visco et al., "Vaginal mesh erosion after abdominal sacral colpopexy," Am. J. Obstet. Gynecol vol. 184, No. 3 pp. 297-303 (2001).

Weber et al., "Anterior vaginal prolapse" review of anatomy and techniques or surgical repair, Obstet. & Gyne., vol. 89, No. 2, pp. 310-318 (1997).

Winters et al., "Abdominal sacral colpopexy and abdominal enterocele repair in the management of vaginal vault prolapse," Urology 56 (Suppl. 6A) pp. 56-64(2000).

* cited by examiner

PELVIC IMPLANT SIZING SYSTEMS AND METHODS

PRIORITY

This application claims priority to and the benefit of U.S. Provisional Patent Application No. 61/546,949, filed Oct. 13, 2011, and U.S. Provisional Patent Application No. 61/546,877, filed Oct. 13, 2011, each of which is fully incorporated herein by reference in its entirety.

FIELD OF THE INVENTION

The present invention relates generally to surgical methods and apparatus and, more specifically, to sizing or gauging features or tools for use with implant systems or kits adapted to treat incontinence or other pelvic disorders.

BACKGROUND OF THE INVENTION

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

There is a desire to obtain a minimally invasive yet highly effective implant or mesh, and systems, device and methods for selecting the appropriate implant to treat incontinence, and/or pelvic organ prolapse and other conditions.

SUMMARY OF THE INVENTION

The present invention describes pelvic implants and methods for treating pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness. Embodiments of the implants can include a tissue support portion and one or more anchors, arms and the like.

The implant can include an indicator gauge or portion included with the structure of the implant, such as a mesh implant, to assist a physician in determining what size implant to insert into the pocket created in a tissue plane of the patient. The flexible gauge can deform a measurable degree when inserted into the tissue plane pocket, where the implant will eventually reside. This deformation of the gauge structure, as the implant is compressed against the margins of the tissue pocket, can cause the relative movement of gauge elements. The gauge can include indicator marks to inform the surgeon or physician whether the pocket is large enough, and what size the implant will need to be to fit appropriately in the pocket region. The present invention will lead to proper implant performance and reduced compilations. Multiple implants can be provided in a kit for the physician.

In certain embodiments, an indication gauge tool can be included in a kit or with the implant system. The tool can include flexible arms, a graduated scale portion and a handle portion. The arms of the tool, e.g., flexible polymer elements, flex and conform to the boundaries or margins of the tissue plane or tissue pocket region when inserted into that anatomical area to provide depth indications and indications as to which sized implant to use.

In other embodiments, pivoting tool can be included to aid in determining the size of implant or mesh needed for a particular tissue repair or support procedure, such as prolapse repair. The pivoting tool can also be utilized in determining if the dissection plane size is adequate for an implant. The tool can include a first handle or arm portion and a second handle or arm portion, with the handles pivotally connected at a living hinge or pivot point. The handles can take on various size and shape configurations—e.g., generally arcuate, boomerang-shaped, C-shaped, L-shaped, and the like.

DETAILED DESCRIPTION OF PREFERRED EMBODIMENTS

Referring generally to FIGS. 1-14, various embodiments of an implant 10 and sizing systems, devices and methods are shown. In general, the implants 10 can include a support portion 12 and anchoring portions 16. Certain embodiments of the implant 10 can be constructed of woven or knitted polymer filaments, while other embodiments of the implant 10 can be constructed into a molded generally planar structure or from a thin generally planar film or sheet material. Examples of acceptable polymer materials available in constructing or forming the implant systems 10 and its components can include polypropylene, polyethylene, fluoropolymers or like biocompatible materials.

The implants 10, and portions thereof, could take on a myriad of different sizes, shapes and configurations depending on the particular treatment application, or deployment and support needs. For instance, certain configurations can be for uterine sparing prolapse repair and others for the post hysterectomy patient.

The various implants 10, structures, features and methods detailed herein are envisioned for use with many known implant and repair devices (e.g., for male and female), features, tools and methods, including those disclosed in U.S. Pat. Nos. 7,500,945, 7,407,480, 7,351,197, 7,347,812, 7,303,525, 7,025,063, 6,691,711, 6,648,921, and 6,612,977, International Patent Publication Nos. WO 2008/057261 and WO 2007/097994, and U.S. Patent Publication Nos. 2011/0124956, 2011/0144417, 2010/0261955, 2002/151762 and 2002/147382. Accordingly, the above-identified disclosures are fully incorporated herein by reference in their entirety.

Figure 1:
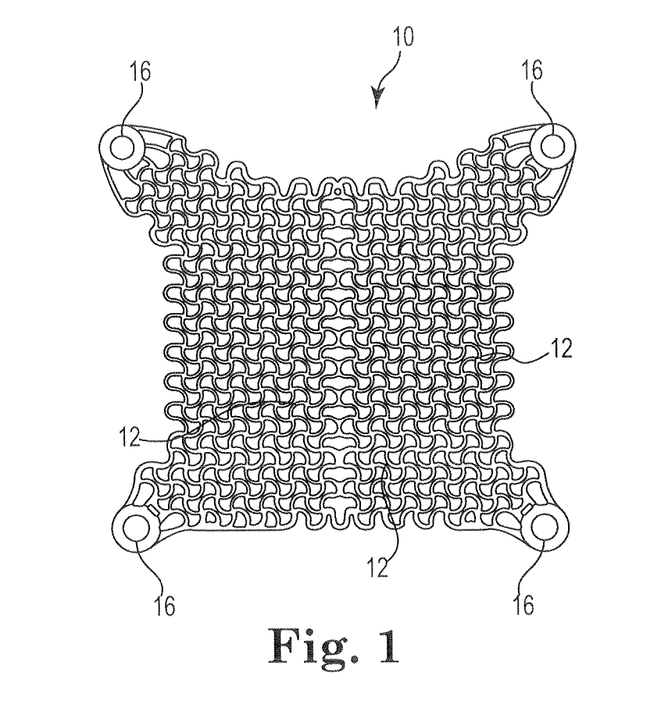
FIGS. 1-2 are top views of support implants, in accordance with embodiments of the present invention.
Figure 2:
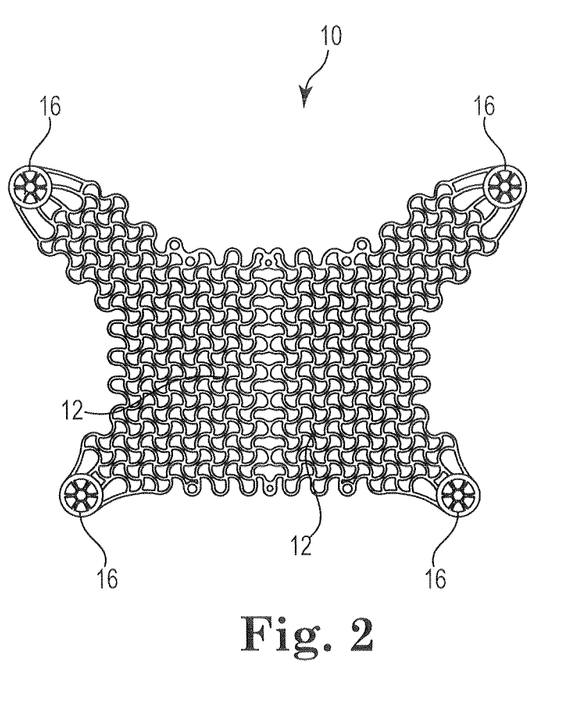
Figure 3:
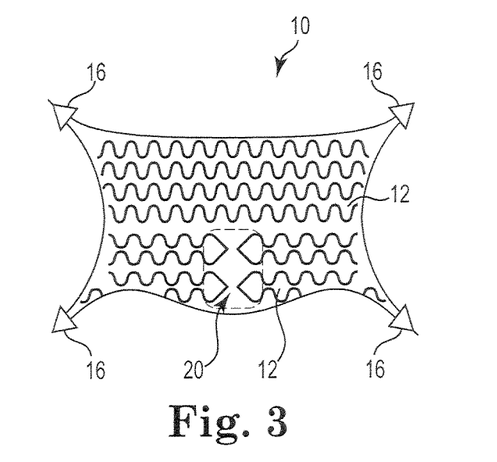
FIG. 3 is a top schematic view of a support implant having a gauge feature, in accordance with embodiments of the present invention.
Figure 4:
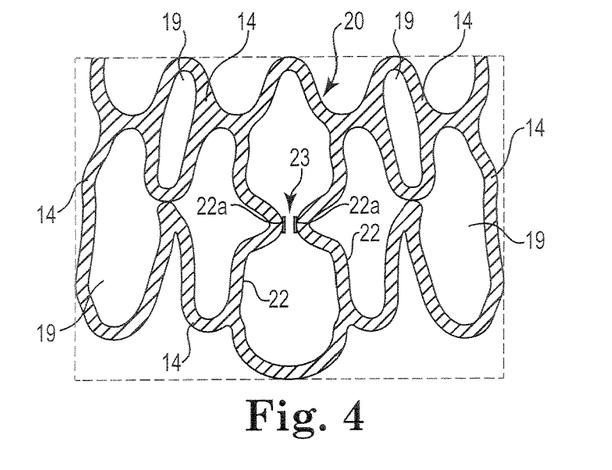
FIG. 4 is a partial close-up view of a gauge feature of an implant, in accordance with embodiments of the present invention.

Referring generally to 1-3, various embodiments of the implant 10 are shown. Portions of the implant 10, such as the support portion 12, can be formed or patterned by way of a polymer molding process to create a unitary homogeneous non-woven, or non-knitted, device or construct. Other embodiments can be formed from an already unitary homogeneous sheet or film via laser cutting, die cutting, stamping and like procedures.

As a result of the manufacturing process, molding or cutting, repeating cells form a lattice structure for at least the support portion 12 of the implant 10. Portions of the implant can be formed into sinusoid, or other waveform or undulating struts 14 to control elongation or compression along single or multiple axes, to define a desirable pattern density with overall reduced surface area, and to control the distribution and shaping from applied loads. The ability to mold, form or cut the struts 14 in a nearly endless array of sinusoidal or like configurations provides an implant 10 that can better tailor or mimic the anisotropic behaviors of physiological tissue.

The anchoring portions 16 can include eyelets, grommets, and/or extending tissue anchors adapted to engage with tissue to assist in positioning the implant 10 within the patient.

In certain embodiments, the patterned struts 14 define a general pinwheel configuration to further define cellular voids 19. The thickness, size and separation of the struts 14 can be modified to create an implant 10 with different surface area and cellular density attributes.

The cross section of non-woven strut members 14 can be generally circular, oval or otherwise formed to have rounded portions with exemplary embodiments of the present invention. This can be an advantage over the bunched woven or knitted filament mesh stands of conventional implants. The rounded portions of the struts 14 of the present invention provide an improved implantation feel and a consistent surface adapted to lay flat and retain its shape against target tissue, and to reduce or eliminate snagging or resistance during deployment and positioning. In addition, it provides a desirable tactile feel and surface for the physician to grasp and manipulate during implantation, and as the implant 10 passes along tissue.

Referring generally to FIGS. 3-6, various embodiments of a mesh or implant 10, such as those depicted herein and/or disclosed in the previously-incorporated references, can include a gauge or sizing indicator feature 20. The gauge feature 20 can be included with or along the structure, e.g., incorporated as part of the implant or separately attached, of the implant 10 to assist a physician in determining what size implant 10 to insert into the pocket created in a tissue plane of the patient where the implant 10 is positioned to provide the desired support treatment. Similarly, the gauge feature 20 can indicate if the tissue plane is correct, too small or too large. The gauge feature 20 can be defined in a portion of the struts 14 cells, or the support portion 12, and is adapted to deform or flex a measurable degree when inserted into the tissue plane pocket, where the implant 10, e.g., the support portion 12, will eventually reside for support. This deformation of the gauge feature 20, as the implant 10 is compressed against the margins of the tissue pocket, causes relative movement of one or more gauge elements 22. The gauge elements 22 are generally spaced from one another and can extend or measure along a distance (e.g., vertical or longitudinal) greater than the other struts 14 of the support portion 12. As such, a well-defined and readable area is provided to measure element 22 deformation and bending to indicate compression and expansion of the implant 10 within the tissue plane or pocket.

A central or other portion of the elements 22 can include a bend portion 22a. In certain embodiments, the bend portions 22a will bend inward toward one another to define a gap 23 therebetween. The degree of the bend, the location of the bend, and the gap 23 distance between the bend portions 22a can vary greatly depending on the level of granular movement and deformation that will need to be measured. In certain embodiments, the elements 22 can be constructed of a thinner or thicker material than the other or surrounding strut members 14 to control the degree of flex and provide a unique bending or flex indicator compared to the rest of the struts 14.

Figure 5:
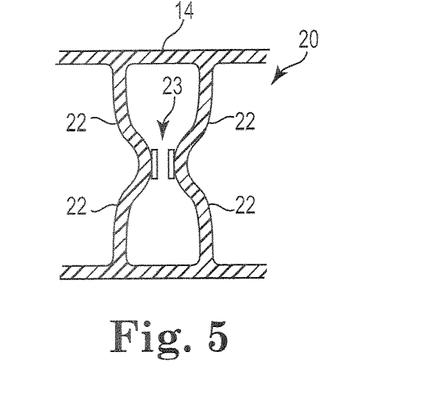
FIGS. 5-6 are close-up views of a gauge feature of an implant, in accordance with embodiments of the present invention.
Figure 6:
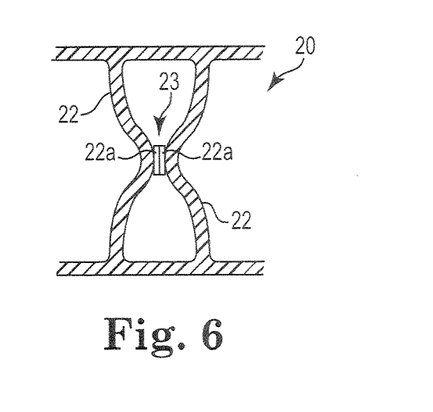

FIG. 5 shows a configuration of the gauge feature 20 where the elements 22 and bend portions 22a are generally not touching, thereby indicating an appropriately sized implant 10 and support portion 12 has been implanted. As such, the displacement of the elements 22 provides a positive indication that the interior pocket is large enough and acceptable. Conversely, FIG. 6 shows the gauge feature 20 in use where the bend portions 22a are touching or at least very close to one another, thereby indicating potential bunching within the tissue plane. This can inform the physician of a negative indication that the interior pocket is not large enough, e.g., the tissue pocket region needs to be increased or enlarged. Alternatively, a smaller implant 10 can be utilized if so desired.

The gauge feature 20 can include indicator mark segments, such as the bend or other structural or visual indicia, to inform the surgeon or physician whether the pocket is large enough, and what size the implant 10 will need to be to fit appropriately in the pocket region. The present invention will lead to proper implant performance and reduced complications.

Figures 7, 8:
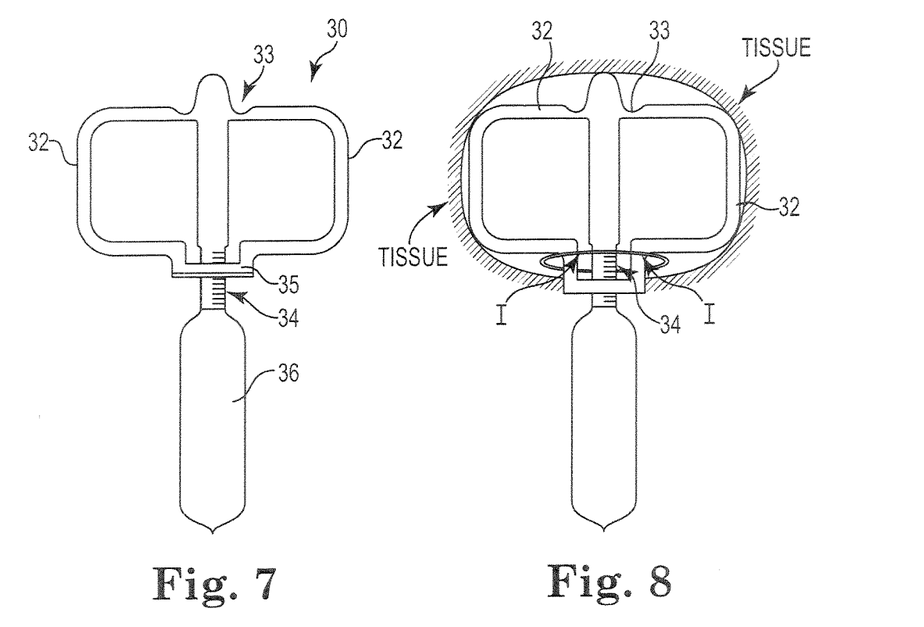
FIGS. 7-8 are views of an indication or sizing tool, in accordance with embodiments of the present invention.
Figure 9:
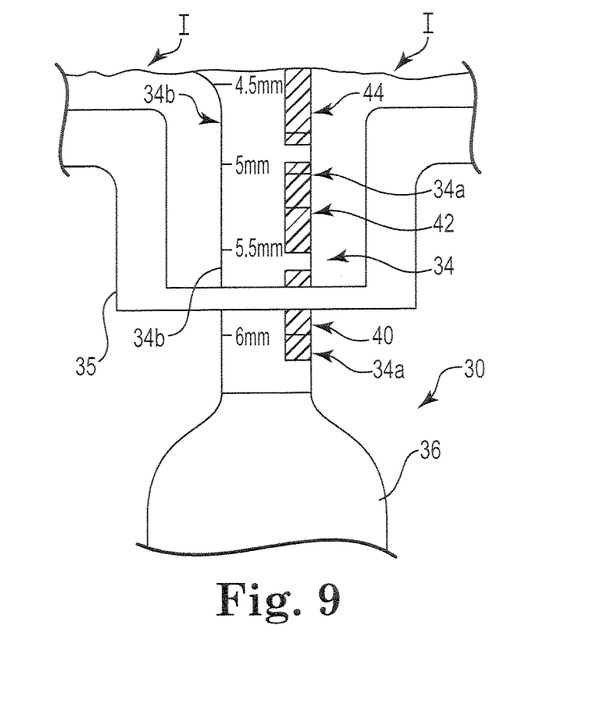
FIG. 9 is a close-up partial schematic view of an indication or sizing tool inserted in an incision, in accordance with embodiments of the present invention.
Figure 10:
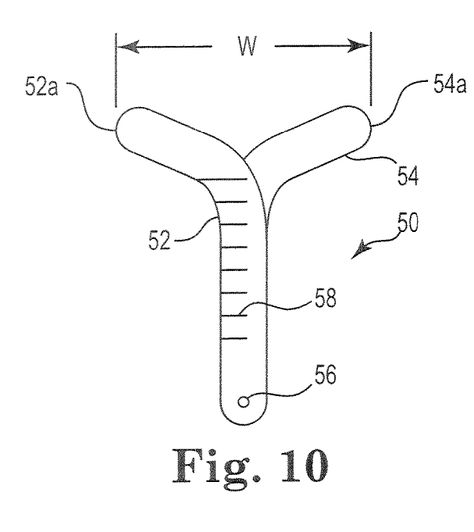
FIGS. 10-11 are views of a pivoting implant sizing tool, in accordance with embodiments of the present invention.
Figure 11:
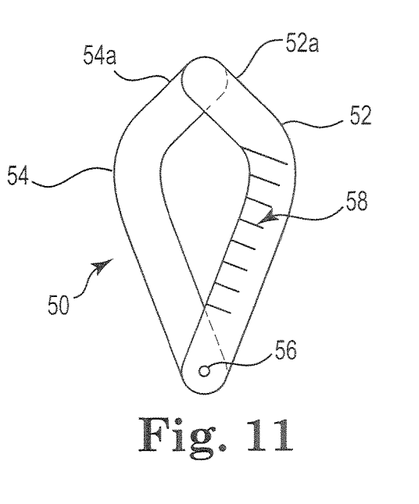
Figure 12:
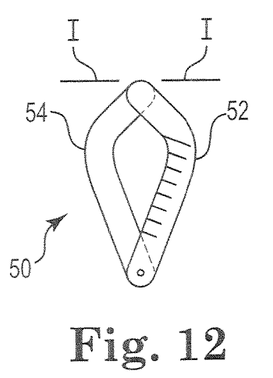
FIGS. 12-14 are schematic views of a pivoting implant sizing tool in use, in accordance with embodiments of the present invention.
Figure 13:
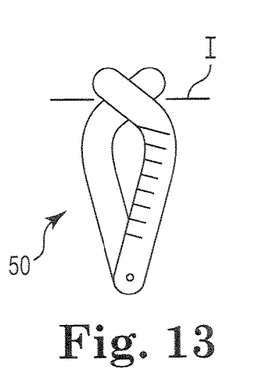
Figure 14:
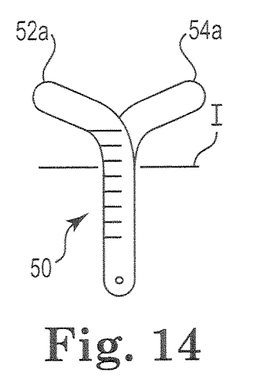

In other embodiments, such as those shown in FIGS. 7-9, an indication gauge tool 30 can be included in a kit or with the implant system 10. The tool 30 can include flexible arms 32, a graduated scale portion 34 and a handle portion 36. The arms 32 of the tool 30, e.g., flexible polymer elements, flex and conform to the boundaries or margins of the tissue plane or tissue pocket region when inserted into that anatomical area. The arms 32 can include a distal hinge portion 33 and a proximal portion 35. The arms 32 can be defined by two generally C-shaped portions extending out from a bar or member operatively connected to the handle portion 36. The amount or degree of flex correspondingly alters or indicates a measurement along the scale portion 34 (FIG. 9). The scale 34 can include two portions: a general implant size scale 34a and tissue depth scale 34b.

For instance, the gauge arms 32 can deform when inserted into the tissue plane pocket where the implant 10 will eventually reside, depending on the boundaries of that pocket. For the implant size scale 34a, certain embodiments can include three size indicators: small 40, medium 42, and large 44. The appropriate implant 10 or implant 10 size is designated based on the bounds of the tissue dissection pocket and the conformity of the arms 32 within that pocket.

Additionally, the depth of the pocket area can be measured with the tissue depth scale 34b. Namely, the measurement along the scale—e.g., 3 mm to 7 mm—can indicate how deep the pocket is from the tip of the tool 30, or hinge portion 33, to the measurement along the scale 34b, including the point at which the incision I aligns with the scale 34b, as shown in FIG. 9.

FIGS. 10-14 depict a pivoting tool 50 to aid in determining the size of implant or mesh needed for a particular tissue repair or support procedure, such as prolapse repair. The tool 50 can also be utilized in determining if the dissection plane size is adequate for an implant 10. The tool 50 can include a first handle or arm portion 52 and a second handle or arm portion 54, with the handles 52, 54 pivotally connected at a living hinge or pivot point 56. The handles can take on various size and shape configurations—e.g., generally arcuate, boomerang-shaped, C-shaped, L-shaped, small, large, and the like. The first handle 52 can include a top portion 52a and the second handle can include a top portion 54a. The top portions 52a, 54a, can arc or otherwise extend away from each other—e.g., in the closed position.

When the handles are in a closed position (FIG. 10), the width of the top portion generally corresponds to the width W of the implant 10 needed or desired. A stop or like feature can prevent the handles 52, 54 from moving past this closed position. The handles pivot so that the tool 50 can be inserted into and removed from an incision I. To insert, the handles 52, 54 can start in an opened position (FIGS. 11-12) and then moved to the closed position (FIGS. 10 and 14) as the tool 50 passes through the incision, such as a vaginal or abdominal incision. For removal, the tool 50 will naturally open as it is pulled back through the incision (e.g., from resistance or biasing). One or more of the handles 52, 54 can include a scale or other measurement indicia 58 so that the physician can measure the prolapsed space to further determine what size and configuration of implant 10 is needed. The pivoting expansion and collapsibility of the tool 50 (e.g., flexible or rigid polymer materials in some embodiments) provides a relatively small tool that can pass through a small incision. Various rounded, flat and like shapes and designs can be employed along portions of the tool 50 to better facilitate insertion, opening, closing and internal cavity passage and usage. An edge or like portion of one of the handle portions 52, 54 can include a shoulder or like feature to prevent the handles 52, 54 from moving past the closed position.

As described and depicted herein, implants 10 of various sizes can be provided. In certain methods, a physician can use his or her fingers to gauge the space the implant 10 will need to fill. A visual reference representing the various implant sizes can be used to compare against the physician's fingers. For example, if the space is three fingers wide and a length from the fingertip to the second knuckle, the physician would place his or her fingers over an appropriate implant 10 to select the correct sized implant 10 for the procedure (e.g., from a kit or selection of two or more implants). In certain embodiments and procedures, a "large" implant 10 is represented by the implant 10 of FIG. 1, and a "small" implant 10 is represented in FIG. 2. Of course, various sizes and shape configurations can be selectively used and labeled to provide the necessary correlation between the support procedure and the appropriate implant 10 to be used.

In certain embodiments, as shown in FIG. 1, a large implant 10 can be provided where the distance between the two top eyelet or anchoring portions 16 be approximately 76 mm, the overall distance between the bottom eyelet or anchoring portions 16 can be approximately 54 mm, and the width or distance from the top eyelet portions to the bottom eyelet portions can be approximately 63 mm. With the smaller implant 10 of FIG. 2, the distance between the two top eyelet or anchoring portions 16 can be approximately 68 mm, the overall distance between the bottom eyelet or anchoring portions 16 can be approximately 54 mm, and the width or distance from the top eyelet portions to the bottom eyelet portions can be approximately 45 mm. Again, various other configurations and dimensional embodiments can be included without deviating from the spirit and scope of the present invention.

The physician can also use this method to determine if the dissection plane is large enough for the implant 10 selected. Numerous optional size and shape configurations can be provided in a kit to facilitate the correct implant 10 selection based on the applicable anatomical and treatment needs. Such a method can eliminate the need to introduce another tool or gauging device into the incision during the procedure.

The implant systems 10, their various components, structures, features, tools, materials and methods may have a number of suitable configurations as shown and described in the previously-incorporated references. Various methods and tools for introducing, deploying, anchoring, sizing and manipulating implants to treat incontinence and prolapse as disclosed in the previously-incorporated references are envisioned for use with the present invention as well. Further, the systems, tools, components or structures disclosed herein can be constructed of compatible materials known to those skilled in the art, including metals, polymers, and the like.

All patents, patent applications, and publications cited herein are hereby incorporated by reference in their entirety as if individually incorporated, and include those references incorporated within the identified patents, patent applications and publications.

Obviously, numerous modifications and variations of the present invention are possible in light of the teachings herein. It is therefore to be understood that within the scope of the appended claims, the invention may be practiced other than as specifically described herein.

The invention claimed is:

1. An implant for treating pelvic prolapse in a patient, comprising:
   a support portion including a plurality of undulating strut members to define a plurality of repeating cells having voids,
   one or more anchoring portions in operative communication with the support portion; and a gauging portion having a first flexible vertical strut element and a second vertical strut element, the second vertical strut element having a same opposing shape as the first vertical strut element, each of the first and second vertical strut elements includes two linear vertical sections and an arcuate section therebetween for each of the respective opposing strut elements, the arcuate sections facing each other and provided generally central along the respective opposing strut element, and a gap therebetween such that the arcuate sections are capable of moving toward and away from one another to provide an indication of whether an interior tissue pocket is acceptable to receive at least the support portion.

2. The implant of claim 1, wherein the one or more anchoring portions includes four anchoring eyelets.

3. The implant of claim 1, wherein the support portion is constructed as a unitary support portion wherein the plurality of undulating strut members are joined at and spanning out from a plurality of fixed junctions.

4. The implant of claim 1, wherein at least the support portion is formed from a polymer molding process.

5. The implant of claim 1, wherein the one or more anchoring portions includes one or more tissue anchors.

6. The implant of claim 1, wherein the first and second flexible vertical strut elements create a void larger than the voids of the repeating cells.

7. The implant of claim 1, wherein the gauging portion is defined in the support portion.

8. The implant of claim 1, wherein the opposing strut elements of the gauging portion are generally thicker than the plurality of strut members of the support portion.

9. An implant kit for treating pelvic prolapse in a patient, comprising:
at least two implants, each of the at least two implants including:
a support portion having a plurality of strut members to define a plurality of void;
one or more anchoring portions in operative communication with the support portion; and
a gauging portion having first and second generally flexible opposing and vertically extending strut elements to define a pair of vertical linear portions and an arcuate portion therebetween for each of the respective opposing strut elements, the arcuate portions facing each other and provided generally longitudinally central along the respective opposing strut element, and a gap therebetween such that the arcuate portions are capable of moving toward one another to provide an indication of whether an interior tissue pocket is acceptable to receive at least the support portion, wherein the arcuate portions include a generally flat tab surface facing each other, wherein the opposing strut elements of the gauging portion are generally thinner than the plurality of strut members of the support portion.

10. The implant of claim 9, wherein the one or more anchoring portions includes four anchoring eyelets.

11. The implant of claim 9, wherein the support portion is constructed as a unitary support portion wherein the plurality of strut members are joined at and spanning out from a plurality of fixed junctions.

12. The implant of claim 9, wherein at least the support portion is formed from a polymer molding process.

13. The implant of claim 9, wherein the one or more anchoring portions includes one or more tissue anchors.

14. The implant of claim 9, wherein the first and second generally flexible opposing strut elements create a void larger than the voids defined by the plurality of strut members.

15. The implant of claim 9, wherein the gauging portion is defined in the support portion.

16. The implant of claim 9, wherein the at least two implants includes at least a first small implant and a second large implant.

17. The implant of claim 9, wherein the at least two implants are formed in a unitary homogeneous sheet or film.

* * * * *